US00PP20217P2

(12) United States Plant Patent
Warren et al.

(10) Patent No.: US PP20,217 P2
(45) Date of Patent: Aug. 18, 2009

(54) *CALLA* LILY PLANT NAMED 'YELLOW JACKET BLZ'

(50) Latin Name: ***Zantedeschia* spp.**
Varietal Denomination: Yellow Jacket BLZ

(75) Inventors: Andrew G. F. Warren, Tauranga (NZ); Jacobus P. Spaans, Tauranga (NZ)

(73) Assignee: Bloomz Ltd, Tauranga (NZ)

( * ) Notice: Subject to any disclaimer, the term of this patent is extended or adjusted under 35 U.S.C. 154(b) by 19 days.

(21) Appl. No.: 12/069,085

(22) Filed: Feb. 7, 2008

(51) Int. Cl.
*A01H 5/00* (2006.01)

(52) U.S. Cl. ..... Plt./490
(58) Field of Classification Search ..... Plt./490
See application file for complete search history.

*Primary Examiner*—Annette H Para
*Assistant Examiner*—S. B McCormick Ewoldt
(74) *Attorney, Agent, or Firm*—Jondle & Associates, P.C.

(57) ABSTRACT

A *calla* lily plant particularly distinguished by yellow spathes, high density maculation of the leaves that is visible from both sides of the leaf and produces 2 to 4 inflorescences per 3-cm tuber, is described.

3 Drawing Sheets

Genus and species: *Zantedeschia* spp.
Variety denomination:
'Yellow Jacket BLZ'.

BACKGROUND OF THE NEW PLANT

The present invention comprises a new and distinct cultivar of *calla* lily, botanically known as *Zantedeschia* spp., and hereinafter referred to by the cultivar name 'Yellow Jacket BLZ'. The new cultivar was asexually reproduced micropropagation by tissue culture resulting from the cross of the female parent 'Sunglow', an unpatented *Zantedeschia* variety and the male parent, 'Pot of Gold', an unpatented *Zantedeschia* variety. 'Yellow Jacket BLZ' is a product of a planned breeding program intended to create new *calla* lily plants with yellow spathes.

The new cultivar was created in Tauranga, New Zealand and has been asexually reproduced repeatedly by micropropagation by tissue culture in New Zealand over a two year period. The present invention has been found to retain its distinctive characteristics through successive propagations.

Plant Breeder's Rights for this cultivar were applied for in New Zealand on Nov. 3, 2006. 'Yellow Jacket BLZ' has not been made publicly available anywhere in the world more than one year prior to the filing date of this application.

SUMMARY OF THE INVENTION

The following are the most outstanding and distinguishing characteristics of this new cultivar when grown under normal horticultural practices in Tauranga, New Zealand.

1. Yellow spathes;
2. High density maculation of the leaves that is visible from both sides; and
3. Produces 2 to 4 inflorescences per 3-cm tuber.

DESCRIPTION OF THE PHOTOGRAPHS

This new *calla* lily plant is illustrated by the accompanying photographs which show the plant habit, mature inflorescence and foliage of the plant. The colors shown are as true as can be reasonably obtained by conventional photographic procedures. The photographs are of a plant approximately 9 weeks-old, after planting.

DESCRIPTION OF THE NEW CULTIVAR

Figure 1:
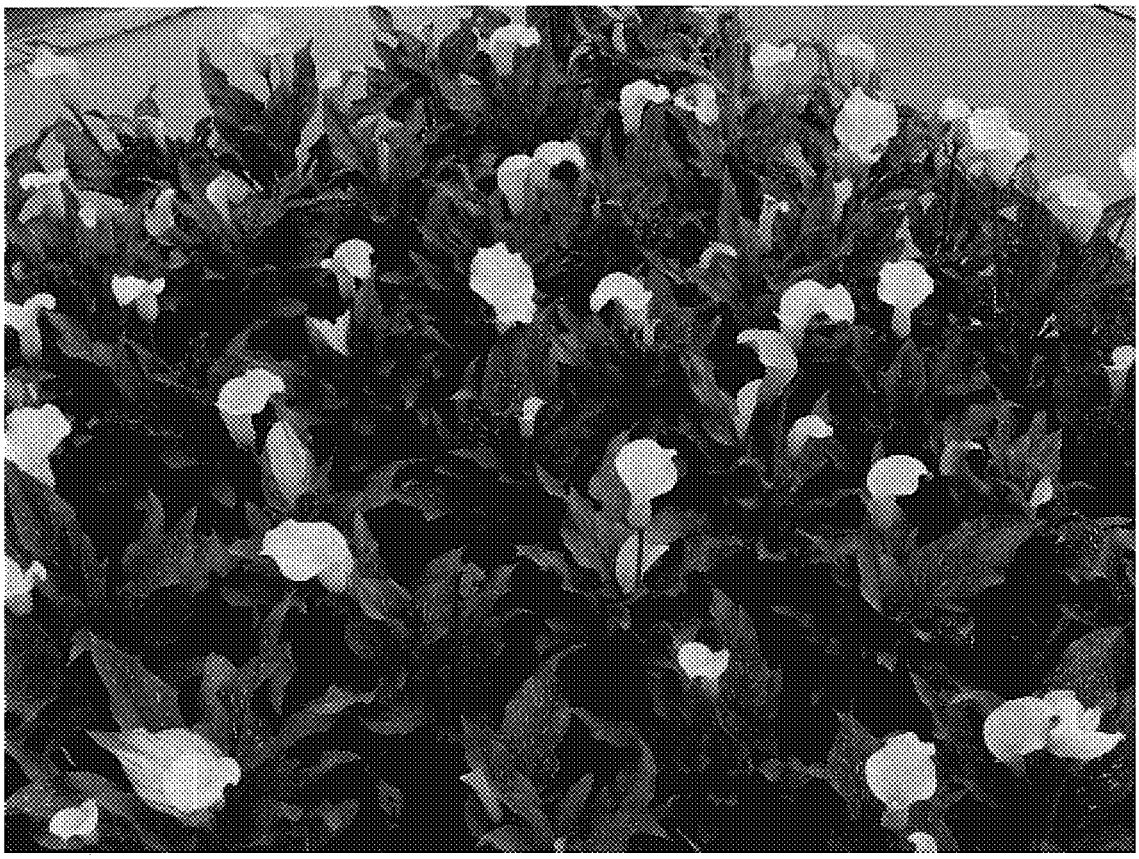
FIG. 1 shows the mature inflorescence and foliage.
Figure 2:
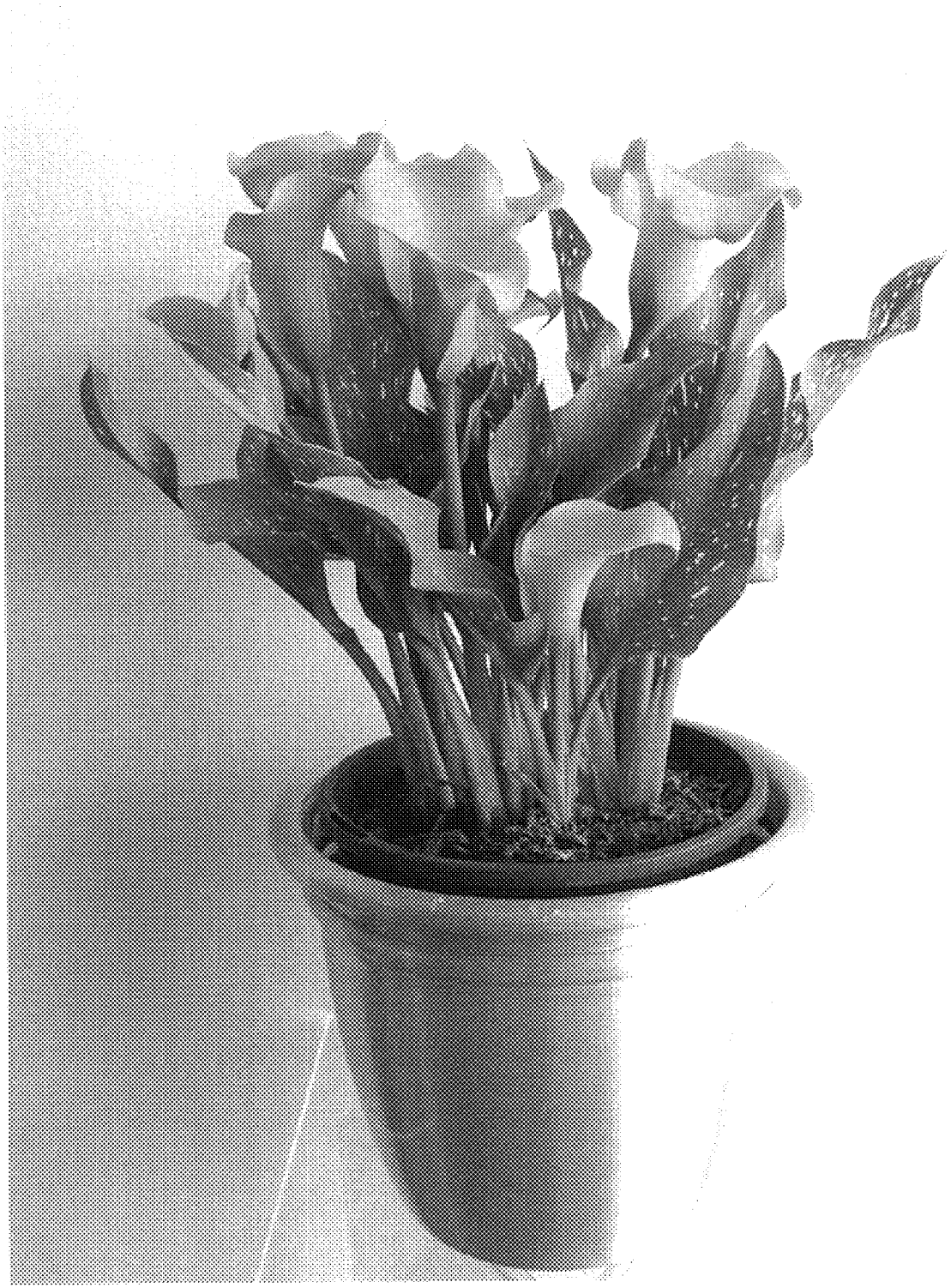
FIG. 2 shows a close-up of the mature inflorescence.
Figure 3:
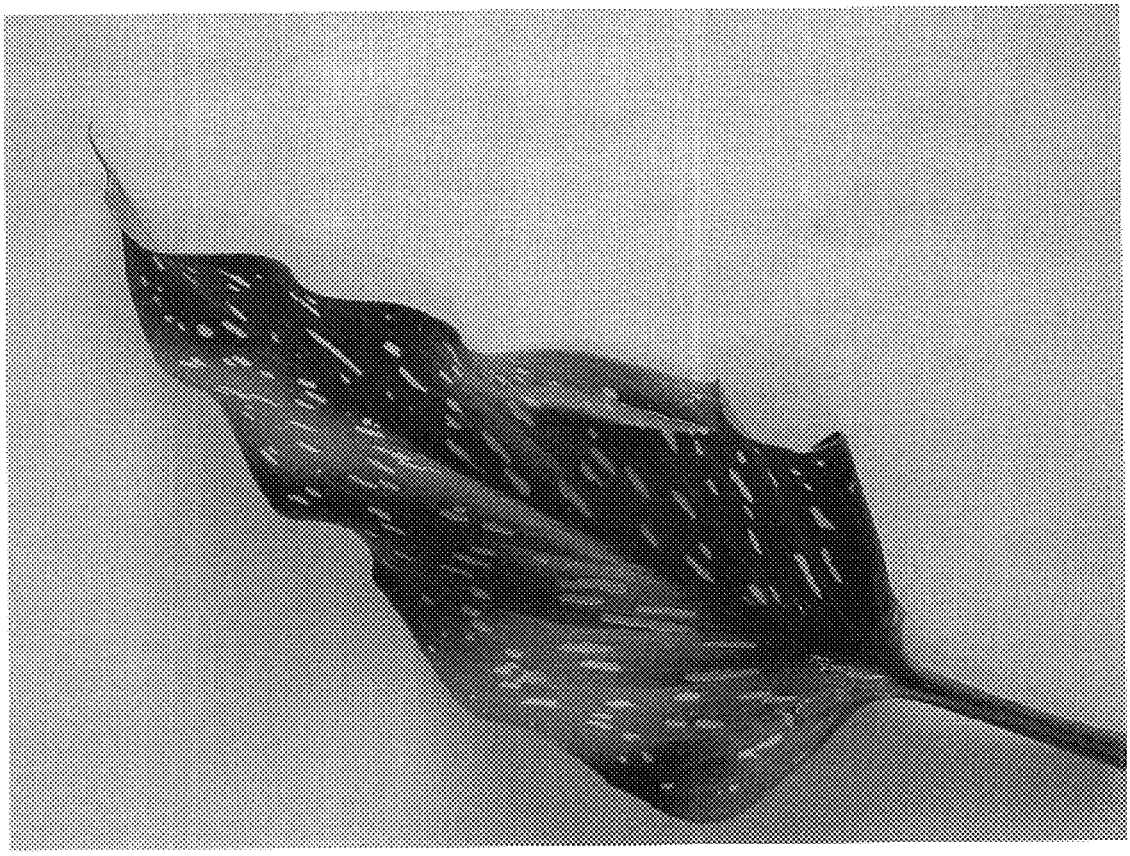
FIG. 3 shows a close-up of the leaf and maculation.

The following detailed description sets forth the distinctive characteristics of 'Yellow Jacket BLZ'. The data that define these characteristics were collected from asexual reproductions carried out in New Zealand. The plant history was taken on plants of two-year-old tubers based on a 3-cm diameter tuber under New Zealand summer conditions. Color references are primarily to the R.H.S. Colour Chart of The Royal Horticultural Society of London (R.H.S.).

DETAILED BOTANICAL DESCRIPTION

Classification:
- *Family.*—Araceae.
- *Botanical name.*—*Zantedeschia* spp.
- *Common name.*—*Calla* lily.

Parentage:
- *Female parent.*—'Sunglow', an unpatented *Zantedeschia* variety having orange/apricot spathes.
- *Male parent.*—'Pot of Gold', an unpatented *Zantedeschia* variety having yellow spathes.

Plant:
- *Form.*—Erect.
- *Height of the leaf canopy above the soil.*—20 cm to 30 cm.
- *Height of top of inflorescence above the soil.*—20 cm to 35 cm.
- *Diameter.*—20 cm to 35 cm.
- *Number of inflorescences per tuber size.*—Tuber diameter 3 cm: 2 to 4. Tuber diameter 4 cm: 3 to 6. Tuber diameter 5 cm: 6+.
- *Time to produce a finished flowering plant.*—6 to 12 weeks depending on the climate and environment.

*Lastingness of the inflorescence on the plant.*—2 to 3 weeks.

Growing points:

*Character.*—Strong.

*Color.*—Upper: RHS 137C. Lower: RHS 146D. Base: RHS 155D.

*Average number.*—2 to 5.

Leaves:

*Size.*—Length: 11 cm to 17 cm. Width: 4 cm to 7 cm.

*Shape.*—Oval (arrow-shaped).

*Apex.*—Acute to apiculate.

*Margin.*—Moderately wavy.

*Margin color.*—RHS 144B (lime green).

*Venation pattern.*—Pinnate.

*Surface texture.*—Leathery.

*Color.*—Upper surface: RHS 146B. Lower surface: RHS 146D.

*Maculation* (*leaf spots*).—General: Maculation is only on the upper surface of the leaf but is visible from the lower surface. Density: High density. Color: RHS 155C.

*Petiole.*—Average number per tuber: 2 to 4. Length: 9 cm to 15 cm. Diameter: 0.6 cm to 1 cm. Texture: Smooth. Character: Strong. Color: Base: RHS 146D. Upper portion: RHS 146C. Sheath: Length: 2 cm to 4 cm. Diameter: 0.6 cm to 0.8 cm. Color: RHS 137C (green).

Roots:

*Color.*—RHS 155D (white).

*Branching.*—Not branched, attached to the top of the tuber at the apices.

Inflorescence:

*Spathe* (*flower body*).—Size: Length: 6 cm to 8 cm. Width: 3 cm to 5 cm. Height: 6 cm to 8 cm. Color: Upper part: RHS 7A. Lower part: RHS 7B. Vein color: RHS 7A. Fragrance: None. Shape: Fluted. Texture: Smooth. Apex: Caudate. Base: Attenuate. Margin: Entire.

*Spadix* (*reproductive organs*).—Size: Length: 2.5 cm to 3.5 cm. Diameter: 0.6 cm to 0.8 cm. Color: Base: RHS 9C. Upper part: RHS 15B Position relative to spathe: Upright. Shape: Elongated. Apex: Rounded.

*Peduncle* (*flower stem*).—Length: 15 cm to 25 cm. Diameter: 0.5 cm to 0.7 cm. Color: Base: RHS 155A. Upper part: RHS 146C. Surface texture: Smooth. Strength: Strong.

Reproductive organs:

*Location of female organs.*—Basal position of the spadix.

*Location of male organs.*—Upper position of the spadix.

*Perianth* (*the floral envelope, calyx and corolla*).—Conspicuous.

*Pollen color.*—RHS 155D (white).

*Stamens.*—Not visible before pollen release.

*Pistil.*—Number: 15 to 25 per spadix. Color: RHS 9C.

Fruit (berries):

*Quantity of berries per plant.*—10 to 16.

*Color.*—RHS 144B.

*Size.*—Length: 4 cm to 5 cm. Width: 2.5 cm to 3.5 cm. Diameter: 0.5 cm to 0.7 cm.

Disease and Insect Resistance:

*Disease resistance.*—No susceptibility to date.

*Pest resistance.*—No susceptibility to date.

COMPARISON WITH PARENTAL AND KNOWN CULTIVARS

When compared to the female parent, 'Sunglow' (unpatented), 'Yellow Jacket BLZ' has yellow spathes, whereas 'Sunglow' has orange/apricot-colored spathes. Additionally, 'Yellow Jacket BLZ' has a higher density of leaf maculation than 'Sunglow'.

When compared to the male parent, 'Pot of Gold' (unpatented), 'Yellow Jacket BLZ' has a more compact plant habit and a more consistent spathe shape than 'Pot of Gold'.

When compared to the commercial variety 'Vermeer' (U.S. Plant Pat. No. 18,281), 'Yellow Jacket BLZ' has yellow spathes, while 'Vermeer' has white and purple spathes.

I claim:

1. A new and distinct cultivar of *calla* lily plant as shown and described herein.

* * * * *